(12) United States Patent
Shemesh et al.

(10) Patent No.: US 9,805,909 B1
(45) Date of Patent: Oct. 31, 2017

(54) METHOD FOR DETECTING VOIDS IN INTERCONNECTS AND AN INSPECTION SYSTEM

(71) Applicant: APPLIED MATERIALS ISRAEL LTD., Rehovot (IL)

(72) Inventors: Dror Shemesh, Hod Hasharon (IL); Lei Zhong, Parker, TX (US)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 0 days.

(21) Appl. No.: 15/271,105

(22) Filed: Sep. 20, 2016

(51) Int. Cl.
  *G01N 23/22* (2006.01)
  *H01J 37/244* (2006.01)
  *G01N 23/225* (2006.01)

(52) U.S. Cl.
  CPC ........ *H01J 37/244* (2013.01); *G01N 23/2252* (2013.01); *H01J 2237/2445* (2013.01); *H01J 2237/24592* (2013.01)

(58) Field of Classification Search
  CPC ........ G01N 23/2252; G01N 23/20025; G01N 23/22; B82Y 10/00; B82Y 40/00; G03F 1/68; G03F 1/36; G03F 1/70; G03F 1/78; G03F 7/2061; H01J 37/3026; H01J 37/3174; H01J 37/28; H01J 37/06; H01J 37/063; H01J 37/07308; H01J 37/145; H01J 37/20; H01J 37/265; H01J 27/02; H01J 27/26; H01J 29/481
  USPC ........ 250/310, 307, 390.07, 492.3; 378/113, 378/124, 44, 45, 46, 48, 50, 83
  See application file for complete search history.

(56) References Cited

U.S. PATENT DOCUMENTS

| | | | |
|---|---|---|---|
| 8,065,094 B2 * | 11/2011 | Statham | G01N 23/2252 250/307 |
| 9,335,283 B2 * | 5/2016 | Geffen | G01N 23/2252 |
| 9,528,949 B2 * | 12/2016 | Kim | G01N 23/20025 |
| 2006/0049349 A1 * | 3/2006 | Shemesh | G01N 23/2252 250/310 |
| 2006/0054811 A1 * | 3/2006 | Shemesh | G01N 23/2252 250/307 |
| 2011/0053056 A1 * | 3/2011 | Fujimura | B82Y 10/00 430/5 |
| 2013/0290913 A1 * | 10/2013 | Fujimura | G03F 1/36 716/53 |
| 2015/0380210 A1 * | 12/2015 | Budach | H01J 37/265 250/307 |
| 2016/0103390 A1 * | 4/2016 | Fujimura | G03F 1/78 430/5 |
| 2016/0104597 A1 * | 4/2016 | Imai | H01J 27/26 250/310 |

* cited by examiner

*Primary Examiner* — David A Vanore
(74) *Attorney, Agent, or Firm* — Kilpatrick Townsend & Stockton LLP

(57) ABSTRACT

An inspection system that includes charged particle optics that irradiate a bottom of a hole with a charged particle beam propagated along an optical axis, an energy dispersive x-ray detector and a processor. The x-ray detector detects x-ray photons emitted from the bottom of the hole and generates detection signals indicative of the x-ray photons. The processor processes the detection signals to provide an estimate of the bottom of the hole.

15 Claims, 16 Drawing Sheets

METHOD FOR DETECTING VOIDS IN INTERCONNECTS AND AN INSPECTION SYSTEM

BACKGROUND OF THE INVENTION

One of the most common defects found in Copper interconnect is buried voids, which is known as a major source of yield loss and reliability degradation.

Detection of Copper voids is an unmet challenge.

Copper film is opaque at visible and UV wavelengths where most of the commercially available optical inspection tools are operating.

In addition—the escape depth of energetic particles such as electron-beam (e-beam) generated signals is limited. High beam energy helps escape in the case of inelastic interaction, but causes concerns over potential damage incurred to low-k film, another essential material for the advanced interconnect technology.

Buried voids close to surface might be detectable by traditional e-beam inspection, which however suffers from high nuisance rate and low capture rate since other contrast mechanisms such as the grainy Copper surface might participate in image formation as well.

There is a growing need to provide systems and methods for efficiently detecting voids in interconnects.

SUMMARY

According to an embodiment of the invention there may be provided a method for detecting voids in an interconnect. The method may include generating or receiving information about a group of points of an upper surface of an object; wherein points of the group of points may be spaced apart from each other; wherein the group of points belong to a group of interaction volumes that may include a group of interconnects; wherein the interaction volumes of the group of interaction volumes may be ideally identical to each other; irradiating the group of points with a charged particle beam thereby causing the group of interaction volumes to interact with charged particles of the charged particle beam; detecting particles resulting from the irradiating of the group of points; wherein the particles may be at least one out of (a) X-ray photons emitted from the group of interaction volumes and (b) backscattered electrons emitted from the group of interaction volumes; generating detection signals that may be indicative of the particles; and processing the detection signals to provide an estimate about a presence of at least one void within at least one of the interconnects of the group of interconnects.

The group of points may consist or include two points.

The group of points may consist or include less than ten points.

The group of points may be included within an area of the upper surface of the object; and wherein the group of points may be less than 1 percent of the points of the area.

Each interaction volume of the group of interaction volumes may include an interconnect and a part of a conductor of a first layer of the object.

The particles may be X-ray photons emitted from the group of interaction volumes and backscattered electrons emitted from the group of interaction volumes.

The particles may be X-ray photons emitted from the group of interaction volumes; and wherein the detecting of the X-ray photons emitted from the group of interaction volumes may be executed by an energy dispersive X-ray (EDX) detector that may be configured to detect x-ray photons emitted from a bottom of a hole and propagate within an angular range that may be defined around an optical axis of the charged particle beam and exceeds ten degrees.

The irradiating of the group of points may include directing the charged particle beam through a charged particle beam optics tip and through an aperture of tip of the EDX detector.

The method may include selecting, based on design data of the object, the group of points.

The method may include selecting, based on design data of the object, the group of points as belonging to interaction volumes that have a probability that exceeds a probability threshold to have interconnects that include one or more voids.

There may be provided an inspection system that may include charged particle optics that may be configured to irradiate a bottom of a hole with a charged particle beam that propagates along an optical axis; an energy dispersive X-ray (EDX) detector that may be configured to (a) detect x-ray photons emitted from the bottom of the hole and propagate within an angular range that may be defined around the optical axis and exceeds ten degrees, and (b) generate detection signals indicative of the x-ray photons; wherein the x-ray photons may be emitted as a result of an irradiating of the bottom of the hole with the charged particle beam; and a processor that may be configured to process the detection signals to provide an estimate of the bottom of the hole.

The charged particle optics may be configured to irradiate the group of points by directing the charged particle beam through a charged particle beam optics tip and through an aperture of tip of the EDX detector.

The processor may be configured to select, based on design data of the object, the group of points.

The processor may be configured to select, based on design data of the object, the group of points as belonging to interaction volumes that have a probability that exceeds a probability threshold to have interconnects that include one or more voids.

A computer program product that stores instructions that once executed by a computer causes the computer to execute the steps of: generating or receiving information about a group of points of an upper surface of an object; wherein points of the group of points may be spaced apart from each other; wherein the group of points belong to a group of interaction volumes that may include a group of interconnects; wherein the interaction volumes of the group may be ideally identical to each other; irradiating the group of points with a charged particle beam thereby causing the group of interaction volumes to interact with charged particles of the charged particle beam; detecting particles resulting from the irradiating of the group of points; wherein the particles may be at least one out of (a) X-ray photons emitted from the group of interaction volumes and (b) backscattered electrons emitted from the group of interaction volumes; generating detection signals indicative of the particles; and processing the detection signals to provide an estimate about a presence of at least one void within at least one of the interconnects of the group of interconnects.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
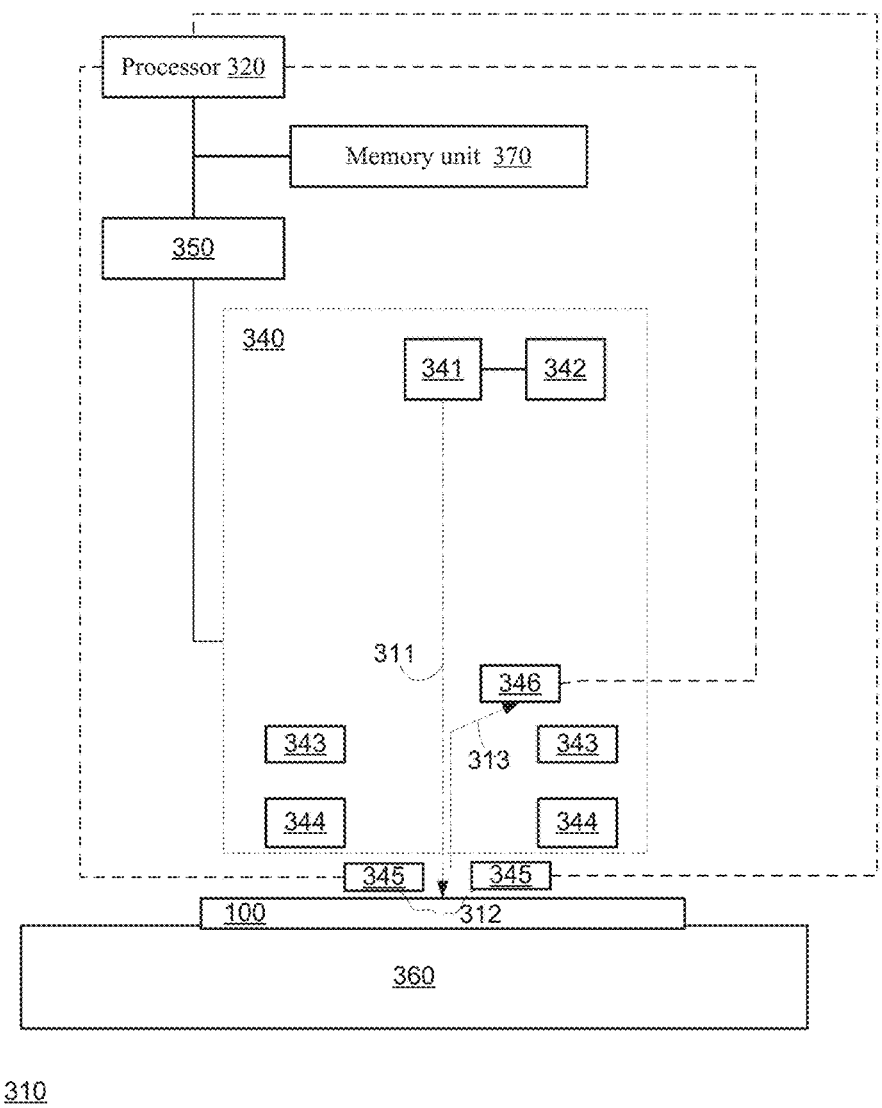
FIG. 1 illustrates an object and a system according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE DRAWINGS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a computer program product that is non-transitory and may store instructions that once executed by a computer result in the execution of the method.

Any reference in the specification to a system should be applied mutatis mutandis to a method that may be executed by the system and should be applied mutatis mutandis to a computer program product that stores instructions that may be executed by the system.

Any reference in the specification to a computer program product should be applied mutatis mutandis to a system capable of executing the instructions stored in the computer program product and should be applied mutatis mutandis to method that may be executed by a computer that reads the instructions stored in the non-transitory computer readable medium.

FIG. 1 illustrates charged particle beam system 310 and an object 100 according to an embodiment of the invention.

Charged particle beam system 310 includes a processor 320, a memory unit 370, a controller 350, an image acquisition module 340 and a mechanical stage 360.

Mechanical stage 360 is configured to move the object 100 in relation to the image acquisition module 340.

The image acquisition module 340 includes an electron source 341, a supply unit 342 for feeding the electron source 341, one or more electron optic components such as lenses 343 and 344, EDX detector 345 and a backscattered electron (BSE) detector 346.

EDX detector 345 may be used for determining a composition of a microscopic element. An energy dispersion x-ray detector collects x-ray photons emitted as a result of an illumination of the microscopic element and generates an energy spectrum. Energy spectrum means any type of information about energy levels at different wavelengths or frequencies along the spectrum. For example—the energy spectrum can be a histogram that displays the number of X-ray photon counts for each x-ray energy level. Measuring X ray energies may help to characterize the element from which an x-ray photon was emitted.

The EDX detector 345 includes an energy analyzer for determining the energy of electrons that are detected by the detector.

It is expected that the number of X-ray photons that are emitted from a interconnect that does not include any void exceeds the number of X-rays photons that are emitted from a interconnect that includes a void. An increase in the volume of void (or voids) of a interconnect may lead to a decrement in the amount of x-ray photons emitted from the interconnect.

By comparing the number of x-ray photons emitted from different interconnects that are ideally identical (identical when there are no voids)—the charged particle beam system 310 may detect voids in interconnects.

Lenses 343 and 344 may be deflecting and/or focusing lenses, objective lenses or any other type of lenses. Lenses 343 and 344 may be magnetic lenses, electrostatic lenses or a combination of both electrical and magnetic lenses.

FIG. 1 illustrates a charged particle beam 311 that is not deflected before reaching lenses 343 and 344. It is noted that the charged particle beam 311 may be deflected once or twice before impinging on object 100. It is noted that the number of deflections can exceed two and that the amount.

In FIG. 1 x-ray photons 312 that are emitted from the object 100 are able to reach EDX detector 345 and BSE 313 are detected by BSE detector 346.

Detection signals generated by EDX detector 345 and BSE detector 346 may be sent, directly or indirectly to processor 320 in order to be processed and detect voids in interconnects.

It should be noted that the image acquisition module 340 may include more than a single EDX detector, more than a single BSE detector, only one or more EDX detectors, only one or more BSE detectors, secondary electron detectors and the like.

It has been found that x-ray photons may be emitted from a region of a interconnect that is deeper than a region of the interconnect from which BSE are emitted.

Figure 2:
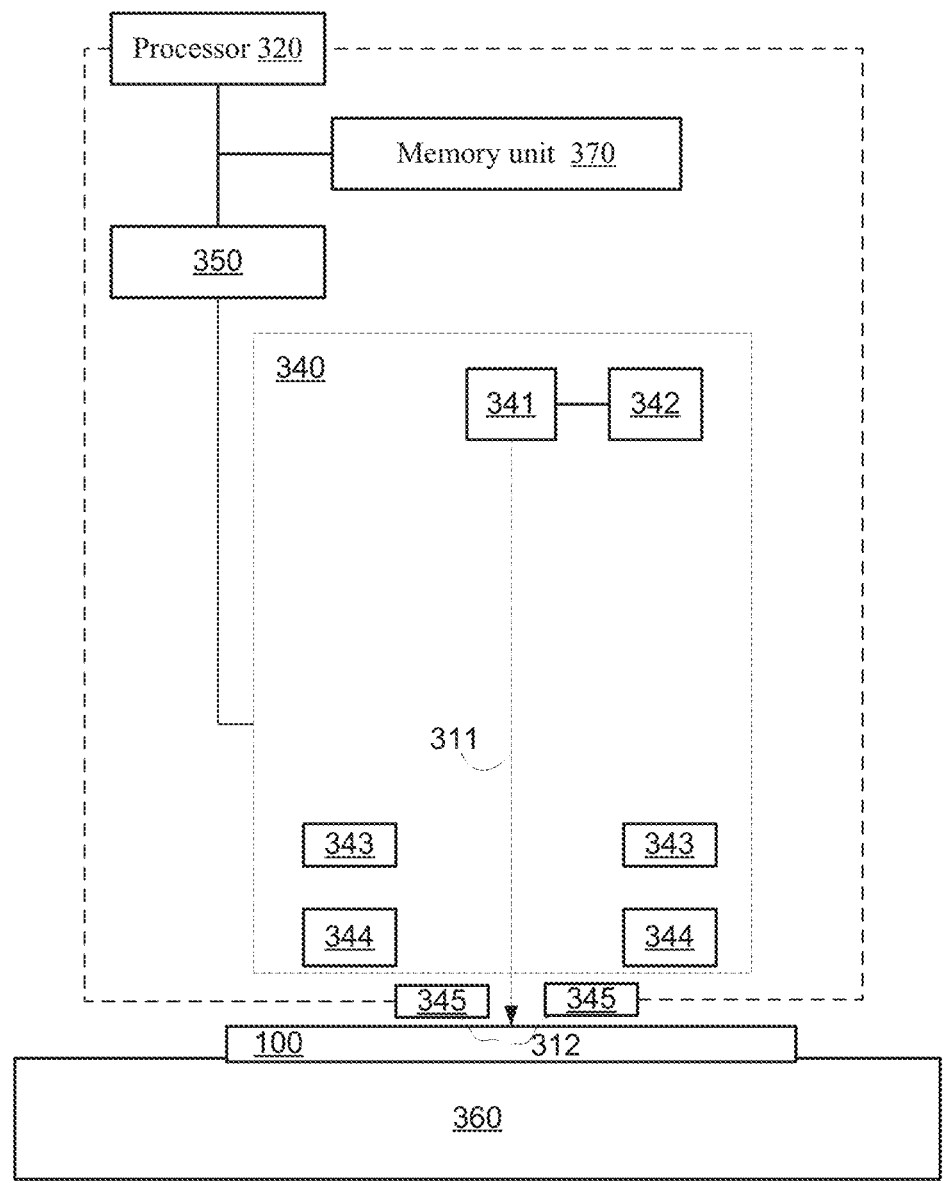
FIG. 2 illustrates an object and a system according to an embodiment of the invention.

FIG. 2 illustrates charged particle beam system 311' and an object 100 according to an embodiment of the invention.

Charged particle beam system 311' differs from charged particle beam system 310 by not including a BSE detector.

Figure 3:
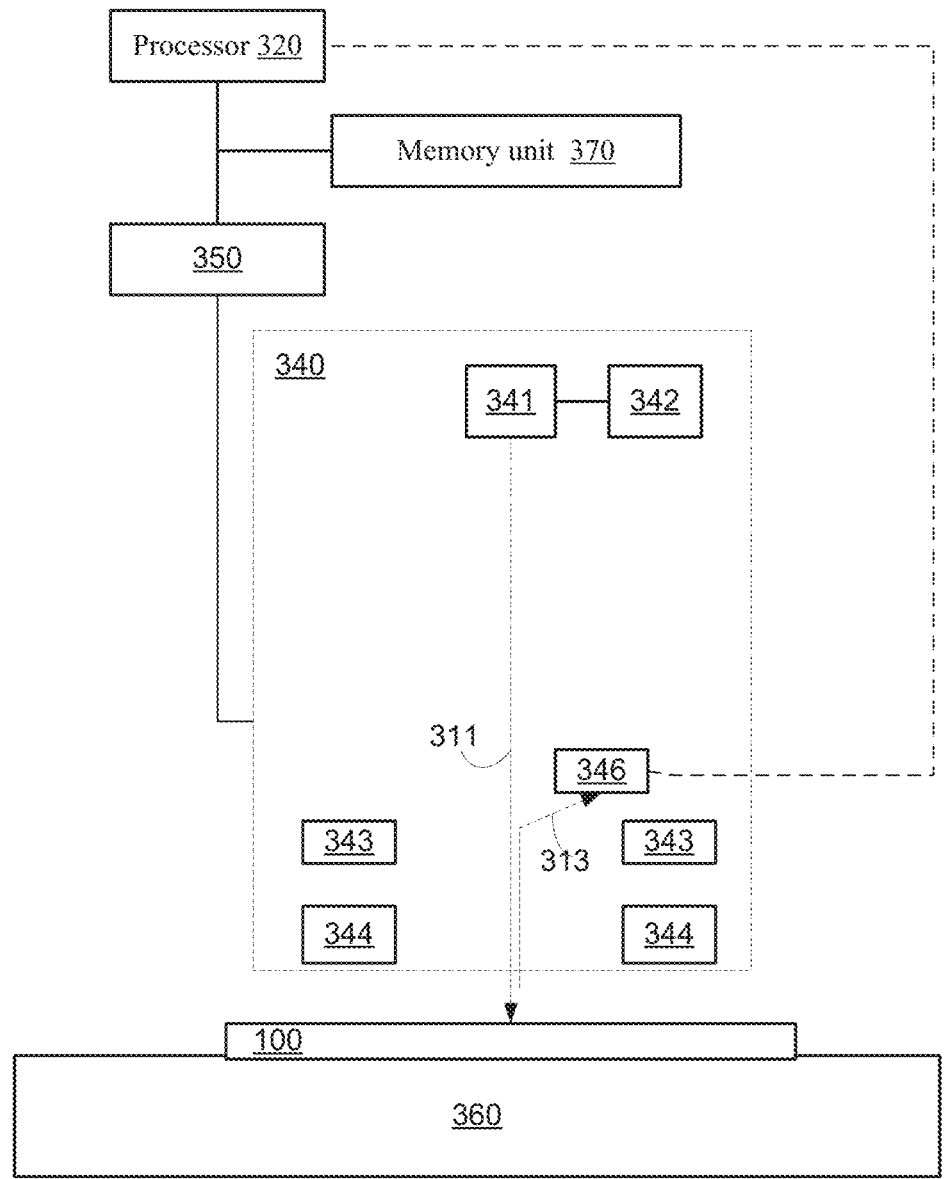
FIG. 3 illustrates an object and a system according to an embodiment of the invention.

FIG. 3 illustrates charged particle beam system 312' and an object 100 according to an embodiment of the invention.

Charged particle beam system 312' differs from charged particle beam system 310 by not including an EDX detector.

Figure 4:
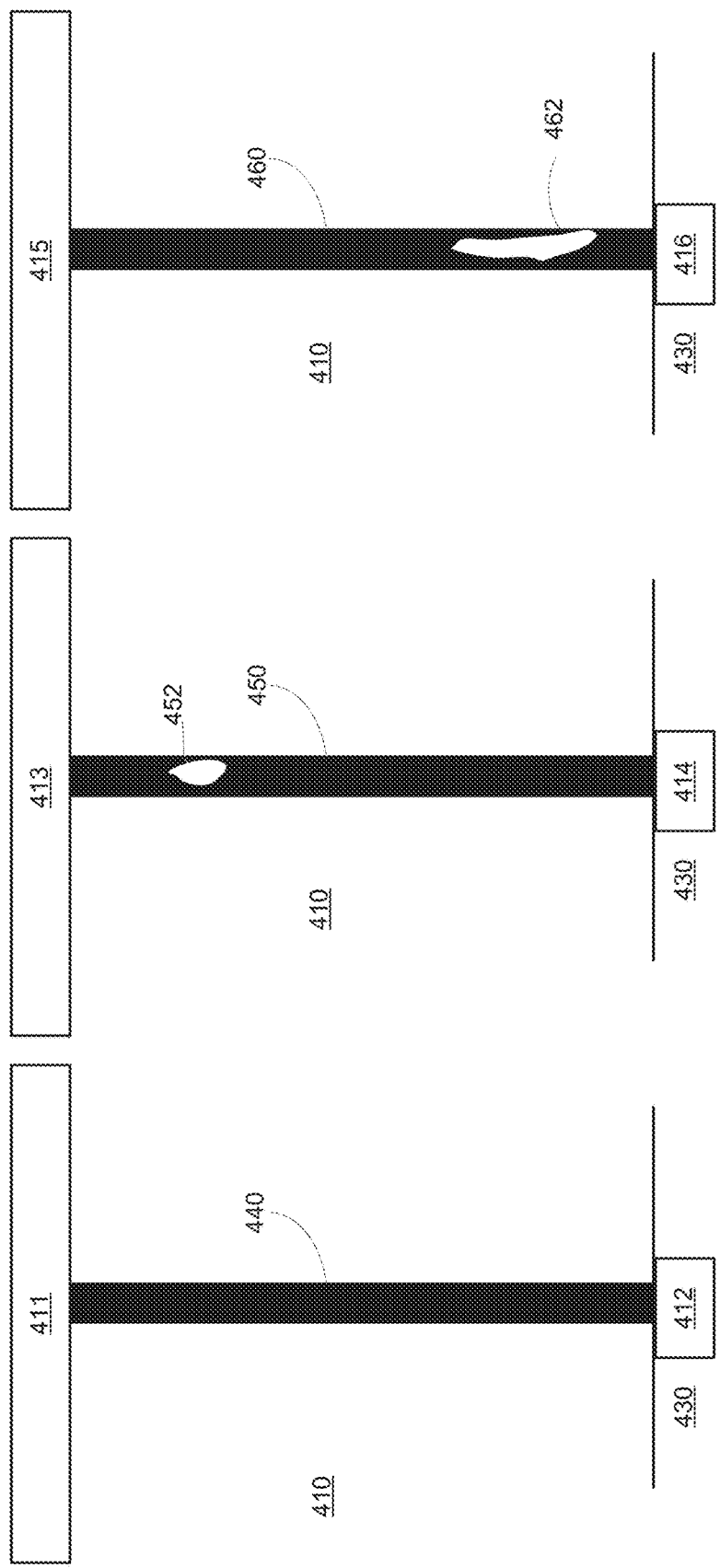
FIG. 4 illustrates interconnects with and without voids.

FIG. 4 illustrates interconnects 440, 450 and 460 with and without voids. Each one of interconnects 440, 450 and 450 is formed within a hole. The hole was formed in dielectric material 410.

Interconnect 440 is electrically coupled between upper conductor 411 and lower conductor 412. Interconnect 450 is electrically coupled between upper conductor 413 and lower conductor 414. Interconnect 460 is electrically coupled between upper conductor 415 and lower conductor 416.

Upper conductors 411, 413 and 415 belong to a metal layer that is positioned above another metal layer 430 that includes lower conductors 412, 414 and 416.

Interconnects 440, 450 and 460 are ideally identical—at the absence of holes they should be identical and should have the x-ray photon peaks in the EDX spectrum and/or have the same BSE count.

Interconnect 440 does not have any voids, interconnect 450 includes a small void 452 that is located at the upper portion of interconnect 450 and interconnect 460 includes a larger void 462 that is located at the lower portion of interconnect 460.

It should be noted that the shape, size, location and number of voids per interconnect may differ from those illustrated in FIG. 4.

Non-limiting examples of the dimensions of the interconnects 440, 450 and 460 are listed below:
a. Diameter may range between 10 nanometer and 1 micron.
b. Depth may range between 100 nanometers and 10 microns.
c. The dielectric material can be made of materials such as but not limited to SiO2 and Si3N4.

Object 100 can be made of materials such as but not limited to Tungsten (W) and Poly silicon.

Figure 5:
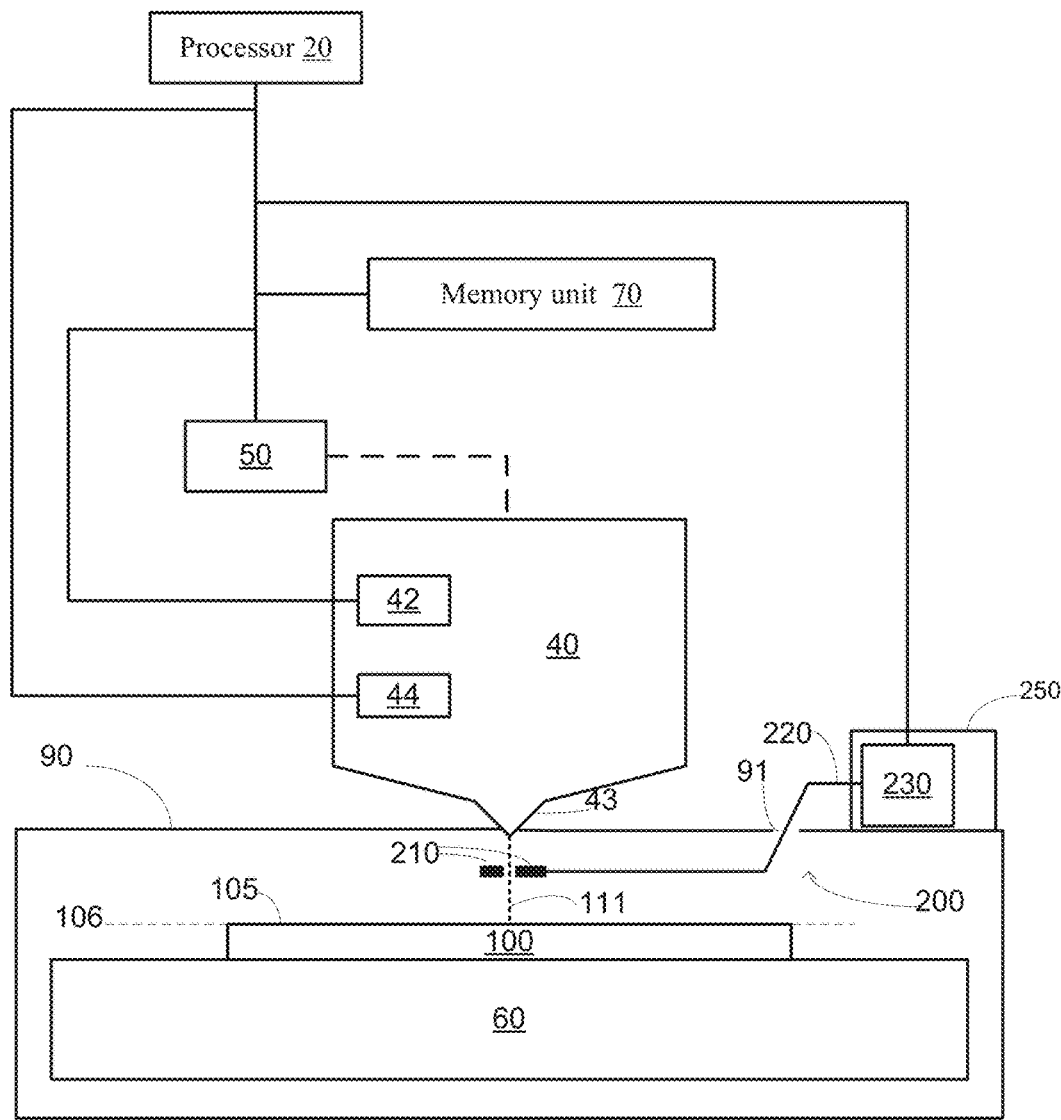
FIG. 5 illustrates an object and a system according to an embodiment of the invention.

FIG. 5 illustrates charged particle beam system 10 and object 100 according to an embodiment of the invention.

Charged particle beam system 10 is illustrated as being a charged particles imager such as but not limited to a scanning electron microscope (SEM) or an electron beam charged particle beam system.

Charged particle beam system 10 includes controller 50, movable stage 60, charged particle beam optics 40, EDX detector 200, EDX detector motion module 250, object chamber 90, memory unit 70 and processor 20.

Controller 50 is configured to control the operation of at least some of the various components of charged particle beam system 10.

Movable stage 60 is configured to support object 100 and move object according to a mechanical scan pattern.

Charged particle beam optics 40 is configured to (a) generate a primary charged particle beam 111, (b) deflect and/or otherwise direct the primary charged particle beam 111 to exit through charged particle beam optics tip 43 to impinge on object 100, (c) detect electrons that are emitted from object.

In FIG. 5 the charged particle beam optics 40 is illustrated as including secondary electron detector 42 and BSE detector 44 that are both in-lens detectors (within the column 45). It is noted that charged particle beam optics 40 may include one or more electron out-lens electron detector (including an out of lens BSE detector), may have only one or more secondary electron detector, may include only one or more backscattered electron detector or may include any combination of electron detectors.

It is noted that the in-lens secondary electron detector 42 may be used when the charged particle beam system inspects areas of the object that are not high aspect ratio holes.

EDX detector motion module 250 is configured to move the EDX detector 200 between a first position and a second position.

Object 100 may be a wafer, a micro-machined object, a solar panel and the like. Object 100 may be relatively large (for example—have a diameter of 300 millimeters) and EDX detector, even when positioned at the second position may be positioned directly above object 100.

Accordingly, the projection of the EDX detector 200 on a plane of object 100 virtually falls on object 100 when the EDX detector 200 is positioned at the first position and when the EDX detector is positioned at the second position.

EDX detector 200 includes EDX detector tip 210, EDX detector conduit 220 and EDX detector amplifier 230. FIG. 5 illustrates EDX detector 200 as being positioned in a first position in which EDX detector tip 210 is positioned between charged particle beam optics tip 43 and object 100. Primary charged particle beam 111 passes through an aperture formed in EDX detector tip 210. EDX detector conduit 220 passes through an object chamber opening 91.

When EDX detector 200 is positioned at the first position, the EDX detector tip 210 is very close (for example—few tenths of nanometers) from the object and thus EDX detector 200 is able to detect x-ray photons that propagate within a large angular range that EDX detectors 200 that are more distant from object 100.

Furthermore—when placing windows on both sides of the aperture—the EDX detector 200 may provide a symmetrical coverage of emitted x-ray photons.

Movable stage 60 may follow a mechanical scan pattern and charged particle beam optics 40 may deflect primary charged particle beam 111 thereby scanning object 100.

X-ray photons emitted as a result of the scanning of object 100 enter the window of EDX detector tip 210 and are detected by an x-ray sensitive element of the EDX detector. The x-ray sensitive element may be a photodiode. The x-ray sensitive element generates detection signals indicative of the detected x-ray photons. The detection signals are sent via EDX detector conduit 220 to EDX detector amplifier 230 and may then be stored in memory unit 70 or processed by processor 20. It is noted that the detection signals may be converted to digital detection signals by EDX detector amplifier 230 or by an analog to digital converter that does not belong to EDX detector amplifier 230.

Processor 20 may be configured to detect voids within interconnects based on the detection signals from EDX detector 200 and/or BSE detector 44.

Figure 6:
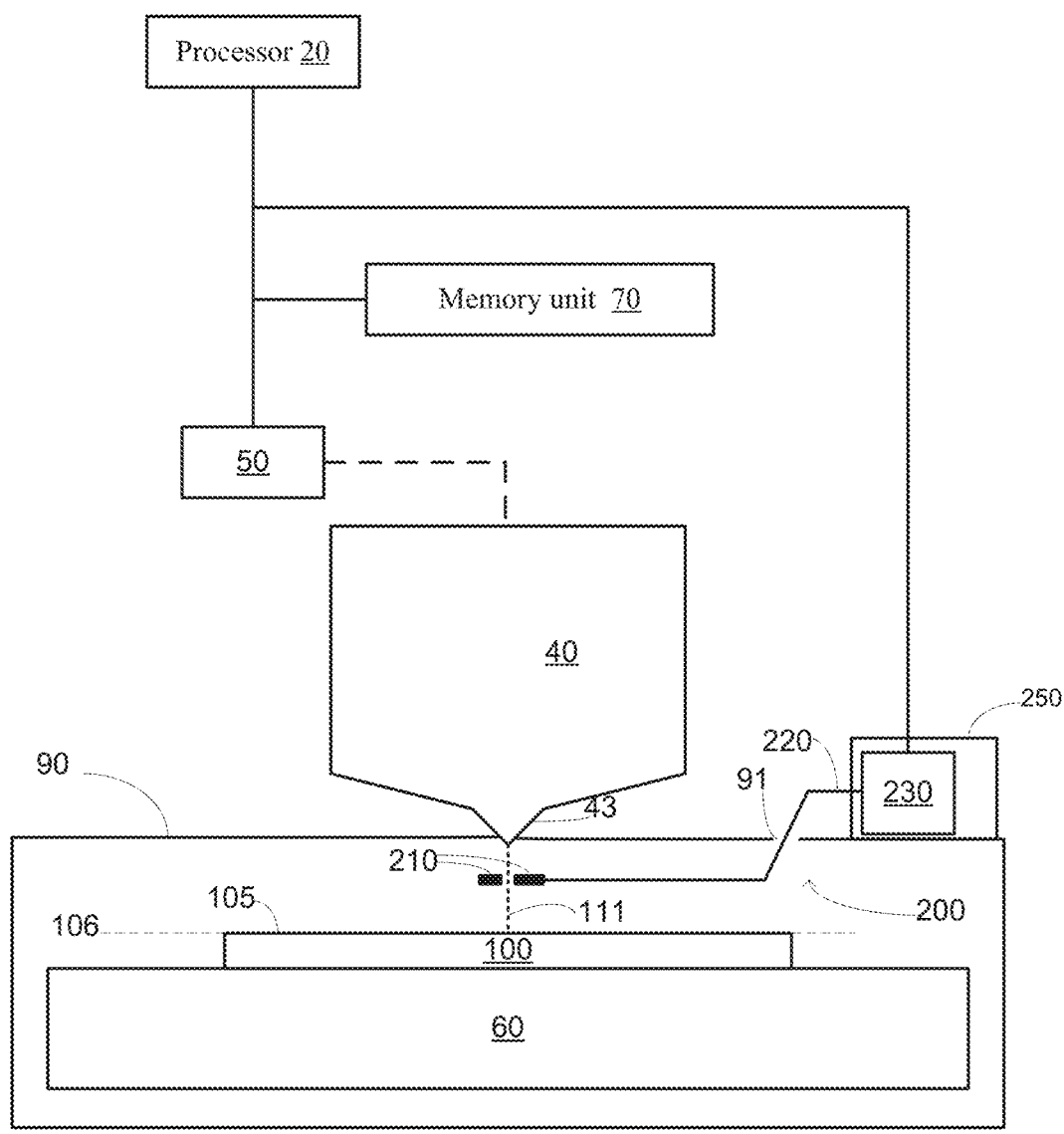
FIG. 6 illustrates an object and a system according to an embodiment of the invention.

FIG. 6 illustrates charged particle beam system 11 and object 100 according to an embodiment of the invention.

Charged particle beam system 11 differs from charged particle beam system 10 by not including a BSE detector.

Figure 7:
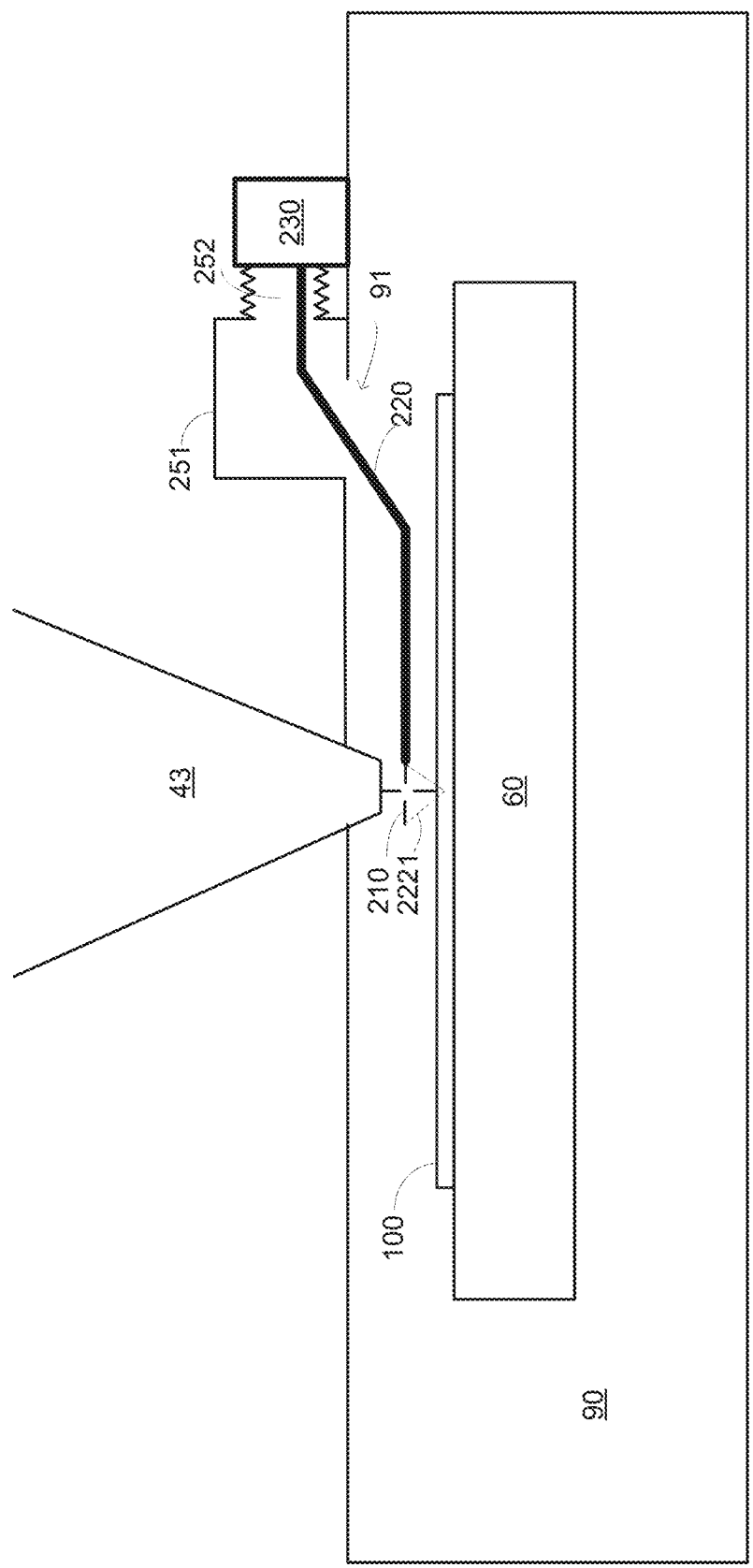
FIG. 7 illustrates an object and a portion of a system according to an embodiment of the invention.

FIG. 7 is a cross sectional view of charged particle beam system 10 and object 100 according to an embodiment of the invention.

EDX detector amplifier 230 is positioned outside object chamber 90 and EDX detector tip 210 is positioned within object chamber 90—at least when EDX detector 200 is positioned at the first position.

Figure 8:
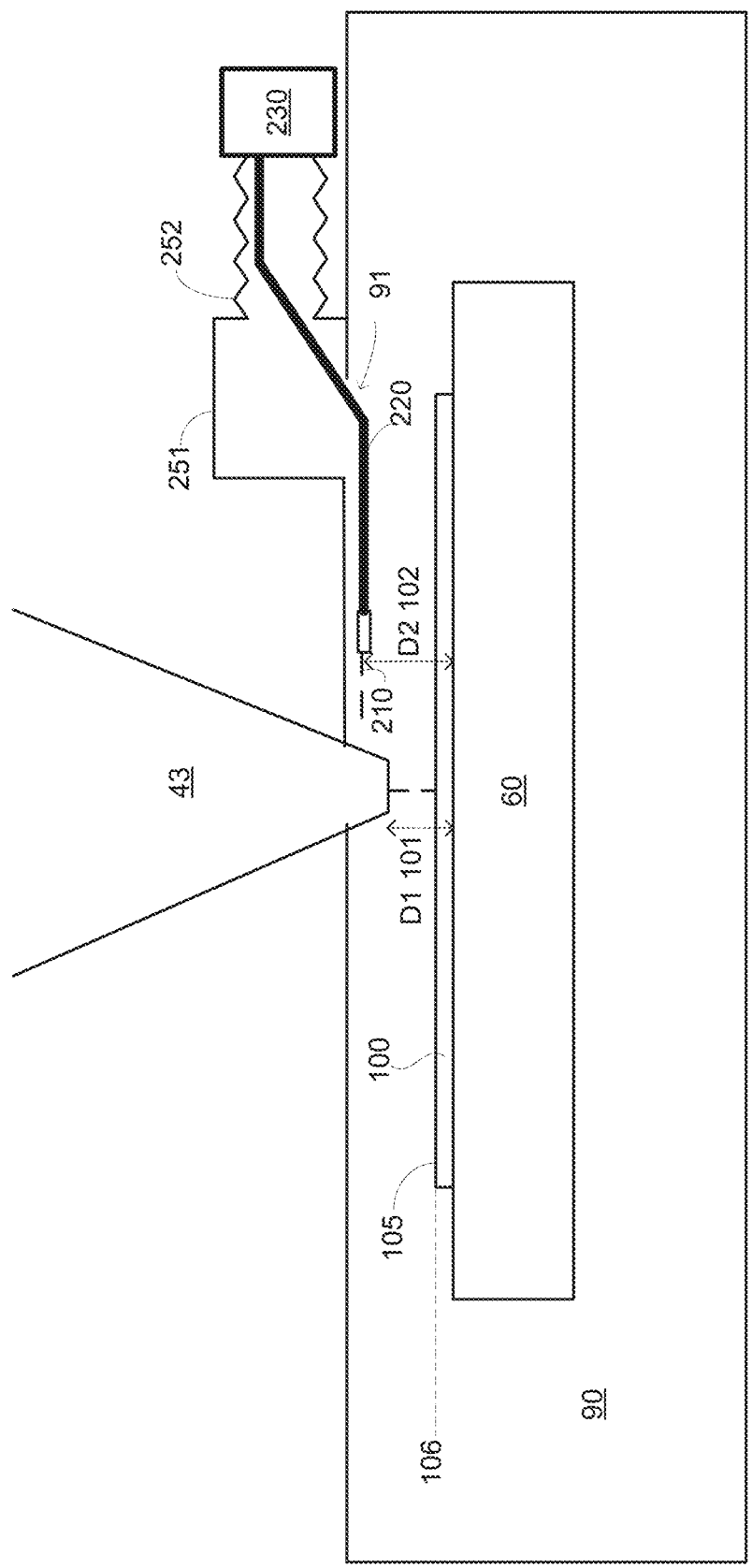
FIG. 8 illustrates an object and a portion of a system according to an embodiment of the invention.

EDX detector tip 210 is coupled to EDX detector amplifier 230 via EDX detector conduit 220. In FIG. 8 the EDX detector 200 is positioned at a first position and the primary charged particle beam passes through an aperture formed in EDX detector tip 210.

FIG. 7 also illustrates the large angular range 2221—wherein x-ray photons that exit within the large angular range 2221 are detected by the EDX detector tip 210. This large angular range allows detecting most of the emitted x-ray photons are provides a reasonable throughput of about a minute per hole—when operating at the first operational mode.

EDX detector conduit 220 passes through object chamber opening 91.

Object 100 is supported by movable stage 60.

In order to maintain very low object chamber pressure the object chamber 90 should be sealed regardless of the position of the EDX detector 200.

The sealing is obtained by including a cover 251 and bellows 252 that surround EDX detector conduit 220 and seal the EDX detector conduit 220 and the object chamber 90 from the environment.

Bellows 252 is flexible and is connected between EDX detector amplifier 230 and cover 251.

FIG. 8 is a cross sectional view of charged particle beam system 10 and object 100 according to an embodiment of the invention.

FIG. 8 illustrates EDX detector 200 as being positioned in a second position in which EDX detector tip 210 is spaced apart from the charged particle beam optics tip 43 and the object 100. EDX detector tip 210 does not interfere with any measurements performed by charged particle beam optics 40.

When in the second position the distance (D1 101) between EDX detector tip 210 and the movable stage 60 exceeds the distance (D2 102) between the movable stage and the charged particle beam optics tip when the EDX detector is positioned at the second position.

The EDX detector 200 can be moved in various manners between the first and second positions. For example, EDX detector 200 can be moved towards the first position by a downwards and leftward movement.

The upper surface of the object is denoted 105 and the plane of object is denoted 106.

Figure 9:
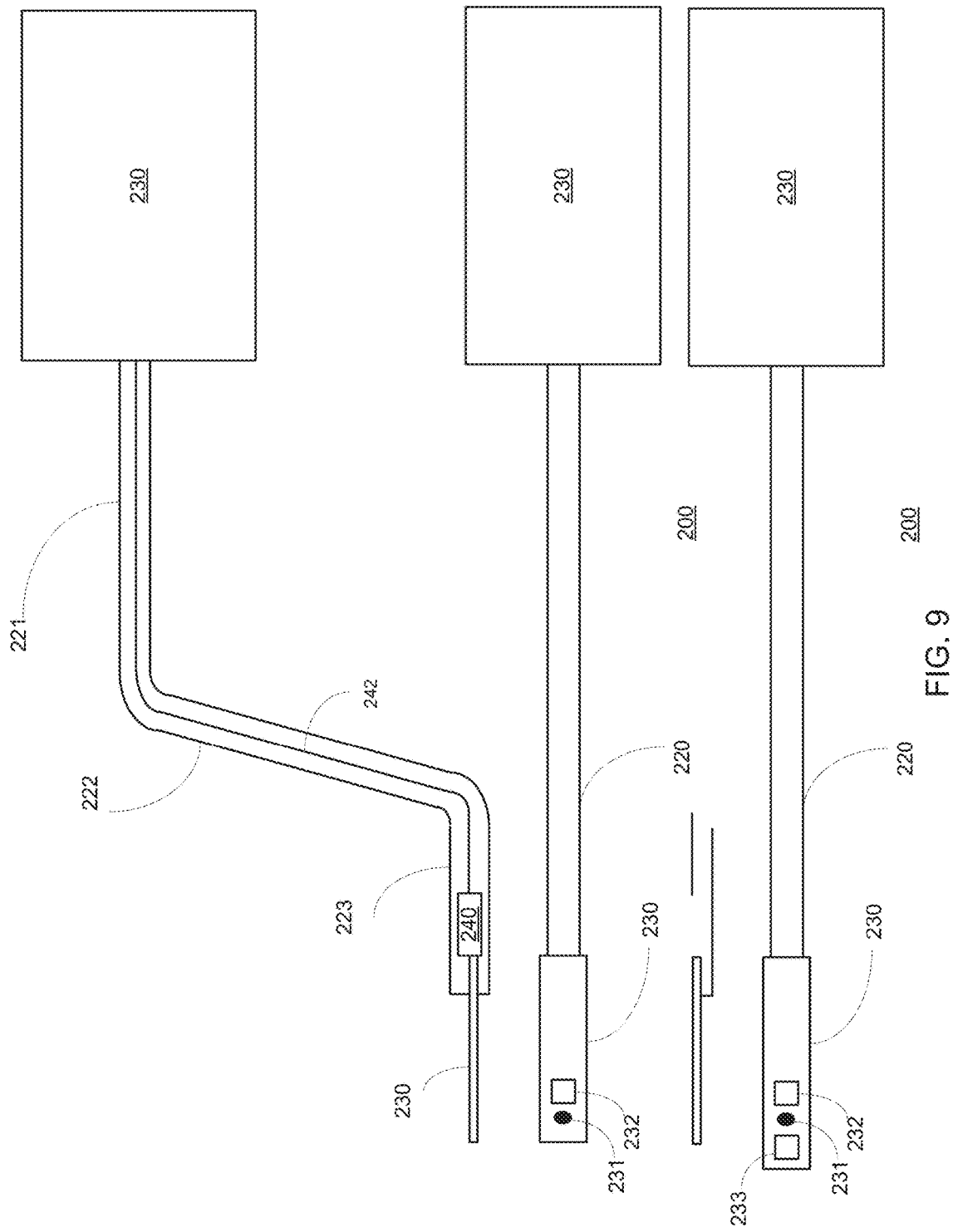
FIG. 9 illustrates a portion of a system according to an embodiment of the invention.

FIG. 9 includes a top view and a side view of EDX detector 200 according to an embodiment of the invention.

EDX detector tip 210 is coupled to EDX detector amplifier 230 via EDX detector conduit 220.

EDX detector tip 210 is illustrates as including aperture 231 and window 232. A primary charged particle beam may pass through aperture 231 when EDX detector 200 is at a first position. X-ray photons emitted from the object pass through window 232 and are detected by x-ray sensitive element 240 of EDX detector 200. The x-ray sensitive element 240 may be position within EDX detector tip 210 but this is not necessarily so.

X-ray sensitive element 240 generates detection signals that are sent, via conductor 242 to EDX detector amplifier 230.

EDX detector conduit 220 is illustrated as including upper horizontal portion 221, lower horizontal portion 223 and sloped intermediate portion 222 that is connected between the upper horizontal portion 221 and the lower horizontal portion 223.

EDX detector conduit 220 may be rigid or elastic. EDX detector conduit 220 may have any shape or size.

FIG. 9 also illustrates an alternative configuration of EDX detector tip 210—that includes multiple windows 232 and 233 that are arranged in a symmetrical manner on both sides of aperture 231.

Figure 10:
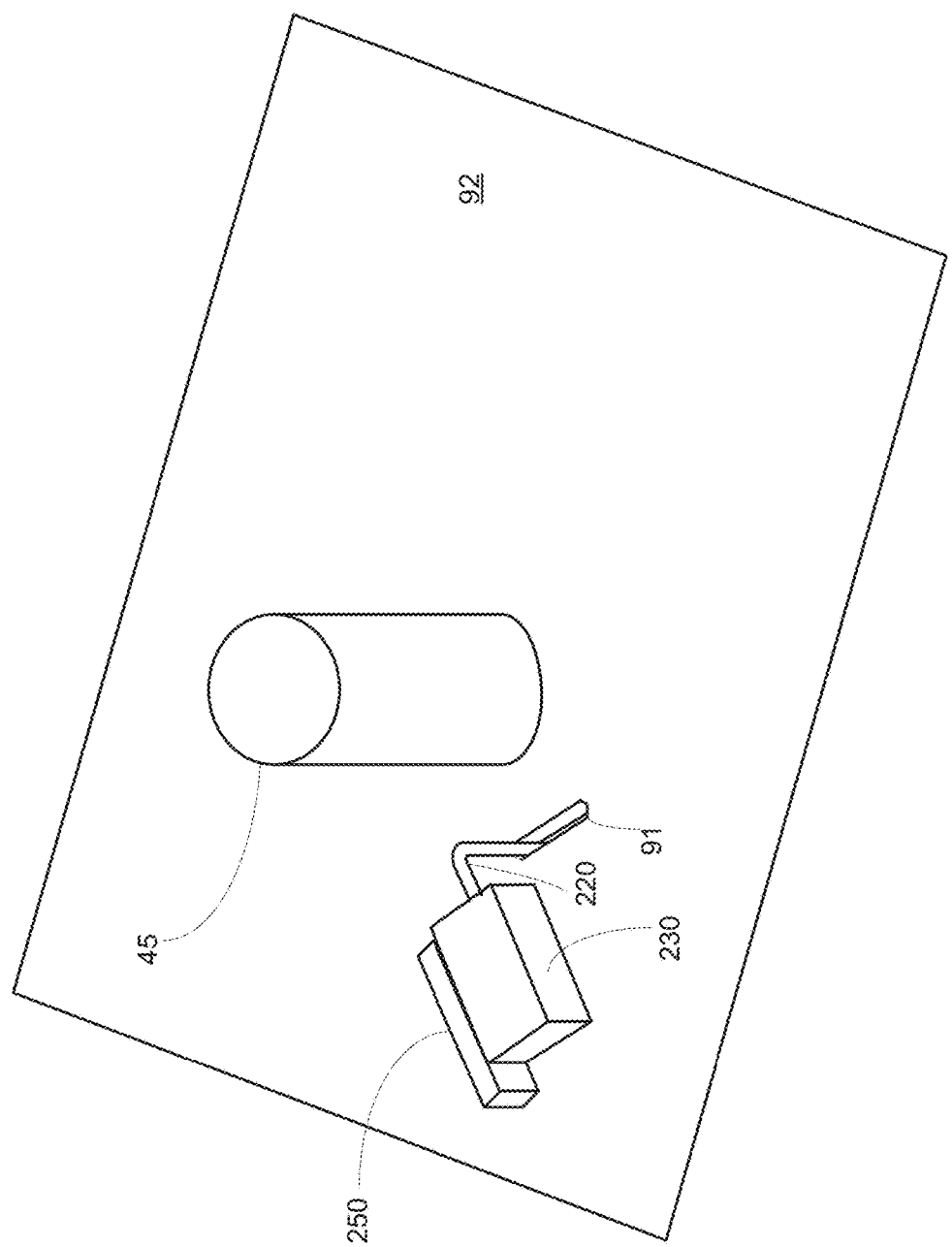
FIG. 10 illustrates a portion of a system according to an embodiment of the invention.

FIG. 10 illustrates an upper facet 92 of object chamber, EDX detector motion module 250, EDX detector amplifier 230, EDX detector conduit 220, object chamber opening 91 and a column 45 of charged particle beam optics 40 according to an embodiment of the invention.

In FIG. 10 the EDX detector 200 is in a first position. Cover 251 and bellows 252 are not shown for simplicity of explanation.

EDX detector motion module 250 contacts the EDX detector amplifier 230 and moves EDX detector amplifier 230 in order to change the position of EDX detector 200.

Figure 11:
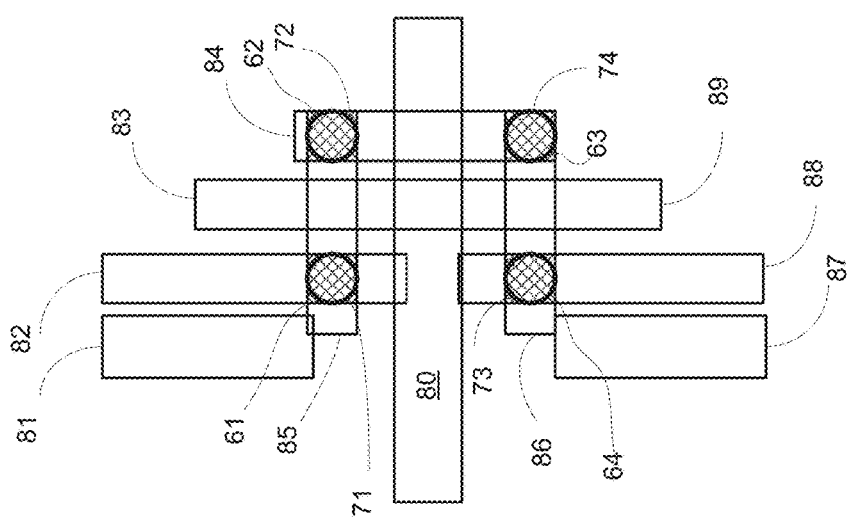
FIG. 11 illustrates points, conductors and interconnects according to an embodiment of the invention.

FIG. 11 illustrates points 71, 72, 73 and 74, conductors 81, 82, 83, 84, 85, 86, 87, 88 and 89 and interconnects 61, 62, 63 and 64 according to an embodiment of the invention.

Conductors 81, 82, 83, 84, 87 and 88 belong to an upper metal layer while conductors 80, 85 and 86 belong to a lower metal layer.

Interconnect 61 is connected between conductors 82 and 85.

Interconnect 62 is connected between conductors 84 and 85.

Interconnect 63 is connected between conductors 84 and 86.

Interconnect 64 is connected between conductors 86 and 88.

Point 71 covers the intersection of conductors 82 and 85—especially covers an area that is positioned immediately above a majority of interconnect 61 but does not extend outside interconnect 61.

Point 72 covers the intersection of conductors 84 and 85—especially covers an area that is positioned immediately above a majority of interconnect 62 but does not extend outside interconnect 62.

Point 73 covers the intersection of conductors 84 and 86—especially covers an area that is positioned immediately above a majority of interconnect 63 but does not extend outside interconnect 62.

Point 74 covers the intersection of conductors 86 and 88—especially covers an area that is positioned immediately above a majority of interconnect 64 but does not extend outside interconnect 64.

Each one of points 71, 72, 73 and 74 is proximate to an edge of one or two conductors.

Figure 12:
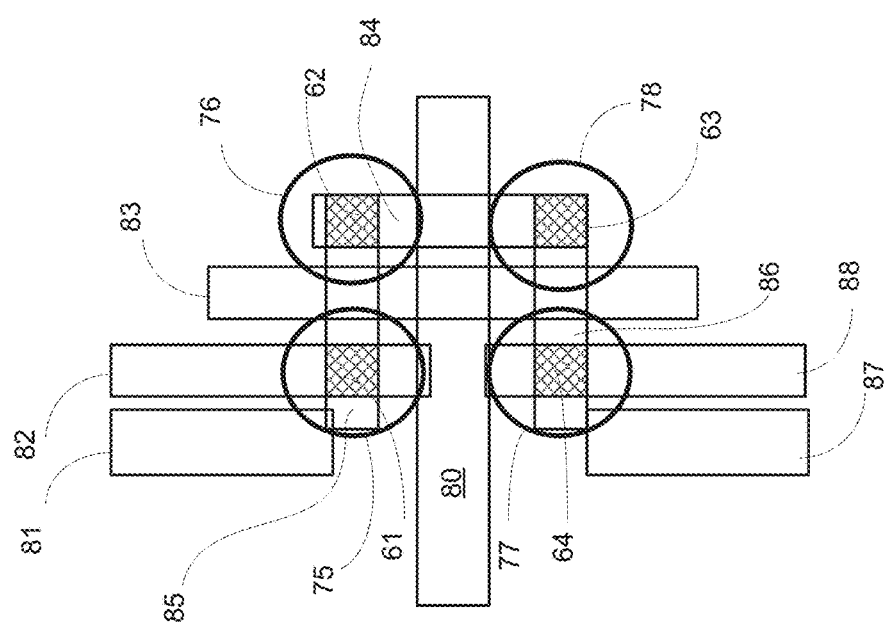
FIG. 12 illustrates points, conductors and interconnects according to an embodiment of the invention.

FIG. 12 illustrates points 75, 76, 77 and 78, conductors 81, 82, 83, 84, 85, 86, 87, 88 and 89 and interconnects 61, 62, 63 and 64 according to an embodiment of the invention.

FIG. 12 differs from FIG. 11 by having points 75, 76, 77 and 78 instead of points 71, 72, 73 and 74.

Points 75, 76, 77 and 78 are larger than points 71, 72, 73 and 73 and cover an area that extends outside interconnects 61, 62, 63 and 64.

Figure 13:
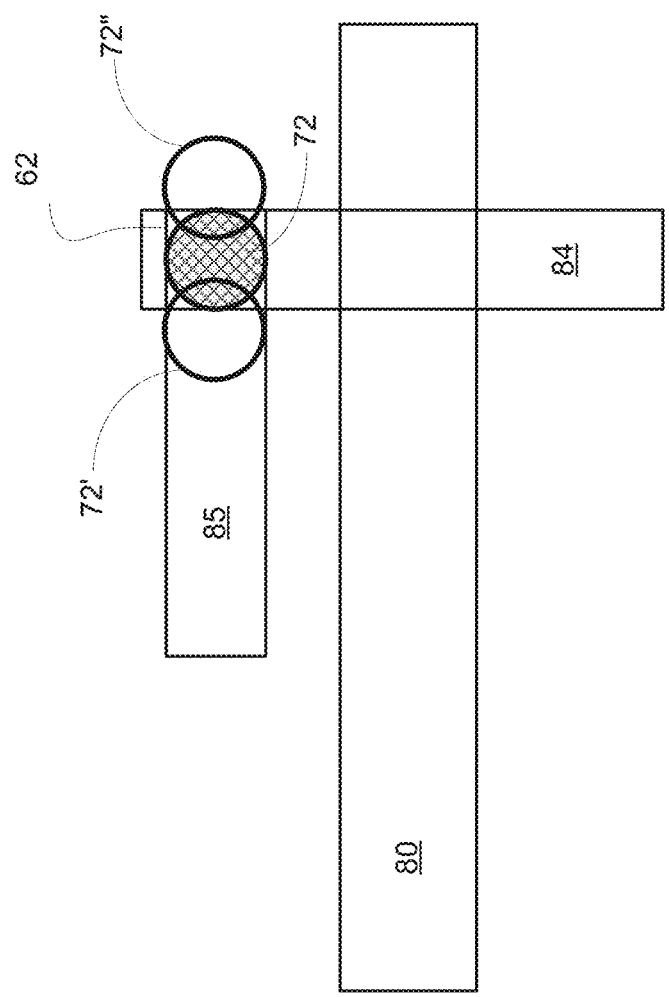
FIG. 13 illustrates points, conductors and interconnects according to an embodiment of the invention.

FIG. 13 illustrates points 72, 72' and 72", conductors 80, 84 and 85 and interconnect 62 according to an embodiment of the invention.

Points 72, 72' and 72" are proximate to each other—and even partially overlap each other. By inspecting different adjacent points, the method may select the point that exhibits the highest copper count—thereby providing a more robust count. A point that exhibits the highest copper count may illuminate the center of the interconnect.

The inspected different points may partially overlap, not-overlap, may be arranged along the conductor, may form a line, may form a circle or any other shape. The number of proximate points may be two, three or more.

Figure 14:
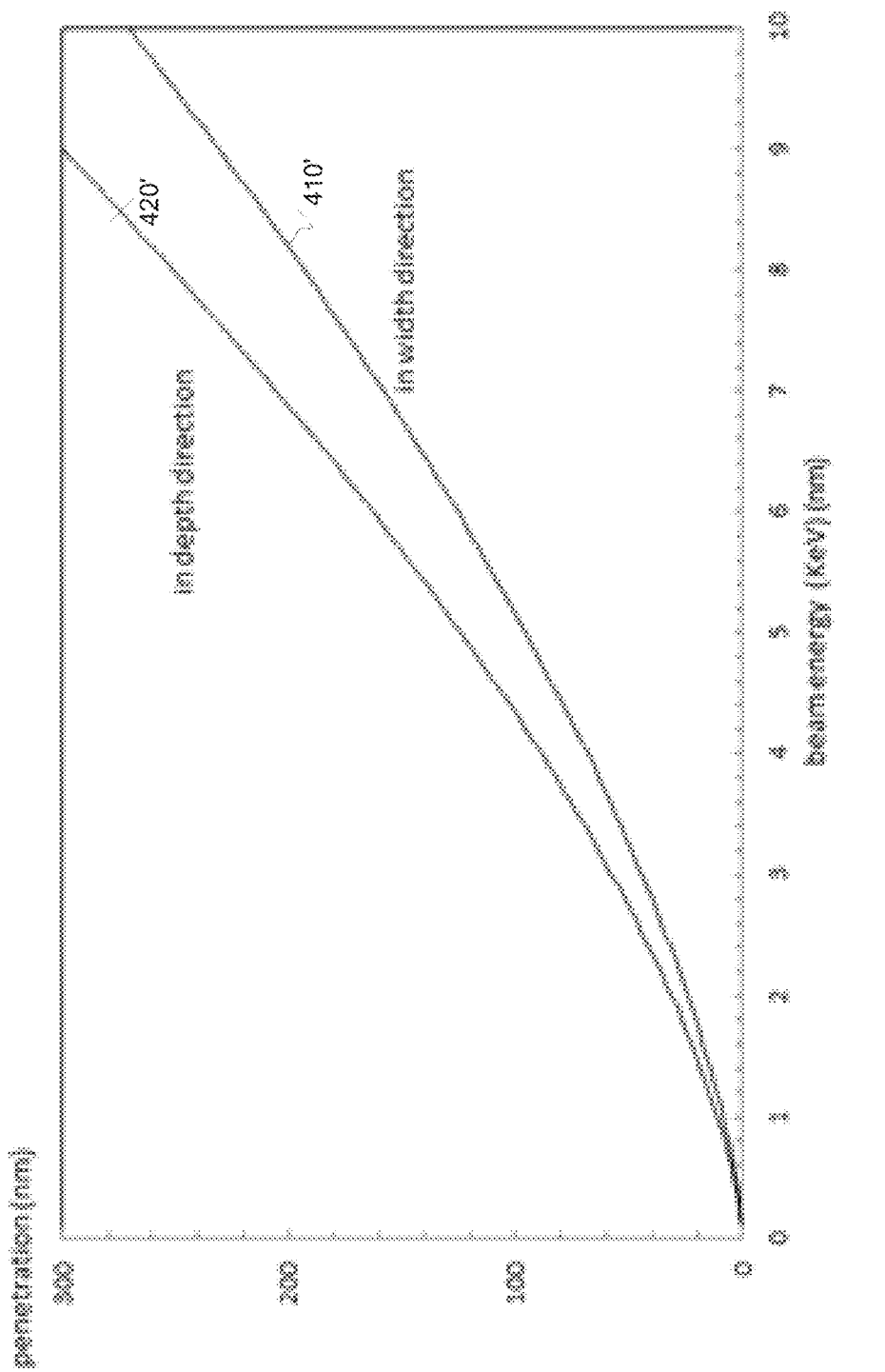
FIG. 14 illustrates a relationship between beam energy and the size of the interaction volume in Copper.

FIG. 14 illustrates a relationship between beam energy and the size of the interaction volume in Copper.

Curves 410' and 420' of graph 400 illustrate a non-linear increment in the penetration depth (Y-axis, nanometers) as a function of an increment of the beam energy (X-axis, Kilo-electron Volts).

Figure 15:
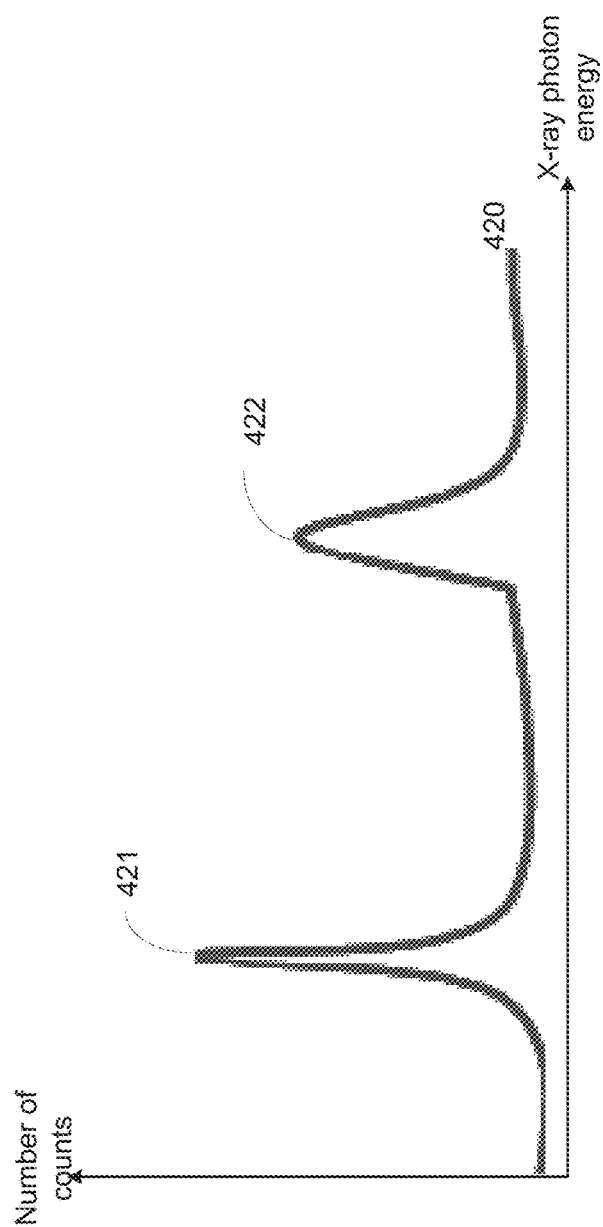
FIG. 15 illustrates an energy dispersion x-ray (EDX) spectrum with peaks resulting from Copper and Silicon.

FIG. 15 illustrates an energy dispersion x-ray (EDX) spectrum 420 with a peak 421 resulting from Copper and another peak 422 resulting from Silicon.

The X-axis represents X-ray photon energy and the Y-axis represents the photon count. The value (photon count) of different spectrums obtained from different points is compared to each other—and points that has a lower photon count (lower Copper peak) are suspected as including defects.

Figure 16:
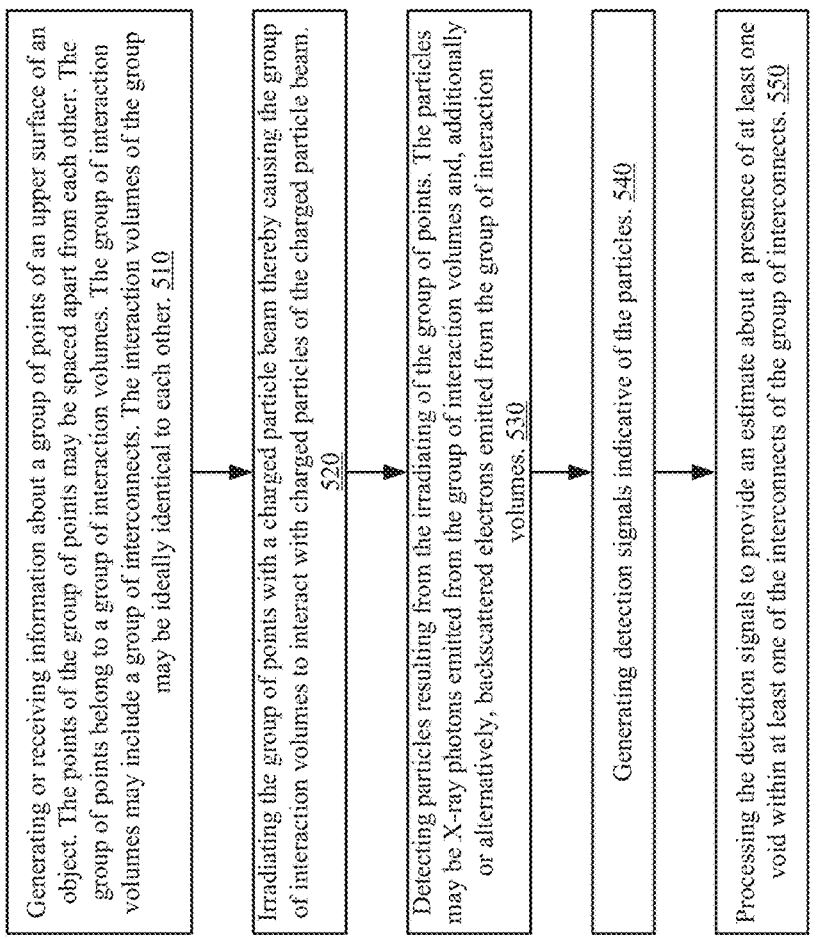
FIG. 16 illustrates a method according to an embodiment of the invention.

FIG. 16 illustrates method 500 according to an embodiment of the invention.

Method 500 is for detecting voids in an interconnect.

Method 500 may start by step 510 of generating or receiving information about a group of points of an upper surface of an object. The points of the group of points may be spaced apart from each other. The group of points belong to a group of interaction volumes. The group of interaction volumes may include a group of interconnects. The interaction volumes of the group may be ideally identical to each other. Accordingly—when manufactured by an ideal and defect-free manufacturing process the interaction volumes may be identical to each other.

Step 510 may include selecting, based on design data of the object, the group of points.

Step 510 may include selecting, based on design data of the object, the group of points as belonging to interaction volumes that have a probability that exceeds a probability threshold to have interconnects that include one or more voids. Non-limiting examples of such points include points that cover an interconnect that is proximate to an end of a conductor. Proximate may be few nanometers (for example less than 10) or be smaller than 10% of the overall length of the conductor.

The group of points may consist of two points, may include two or more points, may include less than ten points or more than ten points.

The points of the group of points may be included within an area of the upper surface of the object. The group of points may cover less than 1 percent of the points of the area.

Each interaction volume of the group of interaction volumes may include a interconnect and a part of a conductor of a first layer of the object. Parts of conductors of the first layer of different interaction volumes may be of a same volume.

Step 510 may be followed by step 520 of irradiating the group of points with a charged particle beam thereby causing the group of interaction volumes to interact with charged particles of the charged particle beam.

Step 520 may also include irradiating multiple sets of points, each set of points is proximate to each other, in order to select, for each set of points, the point that best represents an interaction volume. See, for example, points Step 520 may be followed by step 530 of detecting particles resulting from the irradiating of the group of points. The particles may be X-ray photons emitted from the group of interaction volumes and, additionally or alternatively, backscattered electrons emitted from the group of interaction volumes.

When the particles are X-ray photons emitted from the group of interaction volumes then step 530 may be executed by an EDX detector that is configured to detect x-ray photons emitted from the bottom of the hole within an angular range that is defined around an optical axis of the charged electron beam and exceeds ten degrees.

Step 530 may include detecting charged particle beam through a charged particle beam optics tip and through an aperture of tip of the EDX detector.

Step 530 may be followed by step 540 of generating detection signals indicative of the particles.

Step 540 may be followed by step 550 of processing the detection signals to provide an estimate about a presence of at least one void within at least one of the interconnects of the group of interconnects.

The processing can be done by a computer, an image processor, a general purpose processor, an analyzer, and the like.

The invention may also be implemented in a computer program for running on a computer system, at least including code portions for performing steps of a method according to the invention when run on a programmable apparatus, such as a computer system or enabling a programmable apparatus to perform functions of a device or system according to the invention. The computer program may cause the storage system to allocate disk drives to disk drive groups.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a non-transitory computer readable medium. All or some of the computer program may be provided on computer readable media permanently, removable or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as flash memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:
1. A method for detecting voids in an interconnect, the method comprises:
   generating or receiving information about a group of points of an upper surface of an object, where points of the group of points are spaced apart from each other and the group of points belong to a group of interaction volumes that comprise a group of interconnects, wherein the interaction volumes of the group of interaction volumes are ideally identical to each other;
   irradiating the group of points with a charged particle beam thereby causing the group of interaction volumes to interact with charged particles of the charged particle beam;
   detecting particles resulting from the irradiating of the group of points; wherein the particles are at least one out of (a) X-ray photons emitted from the group of interaction volumes and (b) backscattered electrons emitted from the group of interaction volumes;
   generating detection signals that are indicative of the particles; and
   processing the detection signals to provide an estimate about a presence of at least one void within at least one of the interconnects of the group of interconnects.

2. The method according to claim 1, wherein the group of points consists of two points.

3. The method according to claim 1, wherein the group of points includes less than ten points.

4. The method according to claim 1, wherein the group of points are included within an area of the upper surface of the object; and wherein the group of points are less than 1 percent of the points of the area.

5. The method according to claim 1, wherein each interaction volume of the group of interaction volumes comprises an interconnect and a part of a conductor of a first layer of the object.

6. The method according to claim 1 wherein the particles are X-ray photons emitted from the group of interaction volumes and backscattered electrons emitted from the group of interaction volumes.

7. The method according to claim 1 wherein the particles are X-ray photons emitted from the group of interaction volumes; and wherein the detecting of the X-ray photons emitted from the group of interaction volumes is executed by an energy dispersive X-ray (EDX) detector that is configured to detect x-ray photons emitted from a bottom of a hole and propagate within an angular range that is defined around an optical axis of the charged particle beam and exceeds ten degrees.

8. The method according to claim 1 wherein the irradiating the group of points comprises directing the charged particle beam through a charged particle beam optics tip and through an aperture of tip of the EDX detector.

9. The method according to claim 1 comprising selecting, based on design data of the object, the group of points.

10. The method according to claim 1 comprising selecting, based on design data of the object, the group of points as belonging to interaction volumes that have a probability that exceeds a probability threshold to have interconnects that include one or more voids.

11. An inspection system, comprising:
   charged particle optics configured to irradiate an object with a charged particle beam that propagates along an optical axis;
   a particle detector configured to detect particles resulting from the irradiating of the object and generate detection signals indicative of the particles, wherein the particles are at least one out of (a) X-ray photons emitted from the group of interaction volumes and (b) backscattered electrons emitted from the group of interaction volumes; and
   a processor configured to:
      (i) generate or receive information about a group of points of an upper surface of the object, where points of the group of points are spaced apart from each other and the group of points belong to a group of interaction volumes that comprise a group of interconnects, wherein the interaction volumes of the group of interaction volumes are ideally identical to each other;
      (ii) control the charged particle optics to irradiate the group of points with a charged particle beam thereby causing the group of interaction volumes to interact with charged particles of the charged particle beam;
      (iii) receive the detection signals from the detector; and
      (iv) process the detection signals to provide an estimate about a presence of at least one void within at least one of the interconnects of the group of interconnects.

12. The inspection system according to claim 11 wherein the charged particle optics is configured to irradiate the group of points by directing the charged particle beam through a charged particle beam optics tip and through an aperture of tip of the EDX detector.

13. The inspection system according to claim 11 wherein the processor is configured to select, based on design data of the object, the group of points.

14. The inspection system according to claim 11 wherein the processor is configured to select, based on design data of the object, the group of points as belonging to interaction volumes that have a probability that exceeds a probability threshold to have interconnects that include one or more voids.

15. A computer program product that stores instructions that once executed by a computer causes the computer to execute the steps of:
   generating or receiving information about a group of points of an upper surface of an object; wherein points of the group of points are spaced apart from each other; wherein the group of points belong to a group of interaction volumes that comprise a group of interconnects; wherein the interaction volumes of the group are ideally identical to each other;
   irradiating the group of points with a charged particle beam thereby causing the group of interaction volumes to interact with charged particles of the charged particle beam;
   detecting particles resulting from the irradiating of the group of points; wherein the particles are at least one out of (a) X-ray photons emitted from the group of interaction volumes and (b) backscattered electrons emitted from the group of interaction volumes;

generating detection signals indicative of the particles; and processing the detection signals to provide an estimate about a presence of at least one void within at least one of the interconnects of the group of interconnects.

\* \* \* \* \*